United States Patent [19]

Pees et al.

[11] Patent Number: 5,965,561
[45] Date of Patent: Oct. 12, 1999

[54] PENTAFLUOROPHENYLAZOLOPYRIMIDINES

[75] Inventors: Klaus Jürgen Pees, Mainz; Peter Liers, Münster-Sarmshein; Cornelia Karla, Ingelheim, all of Germany

[73] Assignee: American Cyanamid Company, Madison, N.J.

[21] Appl. No.: 09/053,808

[22] Filed: Apr. 2, 1998

Related U.S. Application Data

[63] Continuation-in-part of application No. 08/729,704, Oct. 7, 1996, Pat. No. 5,817,663.

[51] Int. Cl.⁶ .................. C07D 487/04; A01N 43/90
[52] U.S. Cl. .................................. 514/258; 544/263
[58] Field of Search ............... 544/263; 514/258

[56] References Cited

U.S. PATENT DOCUMENTS 4,567,263  1/1986  Eicken ..................... 544/263

FOREIGN PATENT DOCUMENTS 550113  7/1993  European Pat. Off. .

*Primary Examiner*—Mark L. Berch
*Attorney, Agent, or Firm*—Timothy J. Babcock

[57] ABSTRACT

The novel compounds of formula I

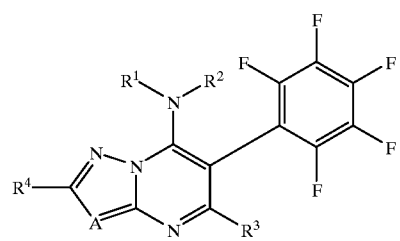

(A and $R^1$ through $R^4$ are defined in the specification) show selective fungicidal activity. The new compounds are obtainable by a new synthetic method and processed with carriers and adjuvants to fungicidal compositions.

18 Claims, No Drawings

PENTAFLUOROPHENYLAZOLOPYRIMIDINES

This is a Continuation-In-Part of application Ser. No. 08/729,704, filed Oct. 7, 1996.

BACKGROUND OF THE INVENTION

This invention relates to certain triazolopyrimidine compounds, a process for their preparation, compositions containing such compounds, a method for combating a fungus at a locus comprising treating the locus with such compounds and their use as fungicides.

EP-A-0071792 discloses compounds of formula I

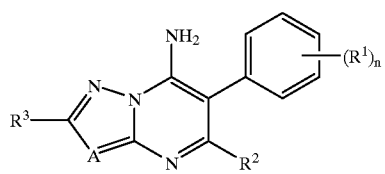

in which $R^1$ represents alkyl, halogen, alkoxy, cyano, cycloalkyl, aryl, aryloxy, arylthio, aralkyl, arylthio, arylalkyl, arylalkyloxy or arylalkylthio each optionally substituted by halogen or alkoxy; or $(R^1)_n$ represents a benzene, indane or tetrahydronaphthalene ring fused with the phenyl ring, aromatic moieties in the above groups being optionally substituted by alkyl, alkoxy, halogen or cyano; n is 1 or 2; $R^2$ and $R^3$ are each hydrogen, alkyl or aryl, A represents a nitrogen atom or a $CR^4$group, and $R^4$ is as $R^2$ but can also be halogen, cyano or alkoxycarbonyl or together with $R^3$ can form an alkylene chain containing up to two double bonds. The compounds are said to be active against various phytopathogenic fungi, especially those of the phycomycete class. However evidence of fungicidal activity is only provided for these compounds against *Plasmopara viticola*, a member of the oomycete class of fungi.

EP 550113-A2 discloses compounds of the general formula

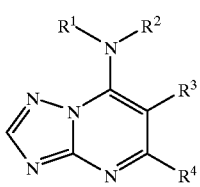

in which $R^1$ represents an optionally substituted alkyl, alkenyl, alkadienyl, cycloalkyl, bicycloalkyl or 2 heterocyclyl group; $R^2$ represents a hydrogen atom or an alkyl group; or $R^1$ and $R^2$ together with the interjacent nitrogen atom represent an optionally substituted heterocyclic ring; $R^3$ represents an optionally substituted aryl group; and $R^4$ represents a hydrogen or halogen atom or a group —$NR^5R^6$ where $R^5$ represents a hydrogen atom or an amino, alkyl, cycloalkyl or bicycloalkyl group and $R^6$ represents a hydrogen atom or an alkyl group. These compounds are said to be active against fungi which are members of the ascomycetes class such as *Venturia inaequalis* and of the hyphomycetes class such as *Alternaria solani* and *Botrytis cinerea*.

SUMMARY OF THE INVENTION

The present invention provides novel pentafluorophenyl substituted azolopyrimidines of formula I

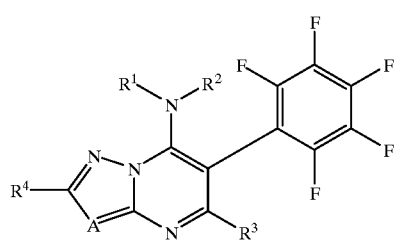

in which
$R^1$ and $R^2$ each independently represent hydrogen or an optionally substituted alkyl, alkenyl, alkynyl, alkadienyl, aryl, heteroaryl, cycloalkyl, bicycloalkyl or heterocyclyl group, or
$R^1$ and $R^2$ together with the adjacent nitrogen atom represent an optionally substituted heterocyclic ring,
$R^3$ represents a hydrogen or halogen atom or a group —$NR^5R^6$, wherein $R^5$ and $R^6$ each independently have one of the meanings given for $R^1$ and $R^2$,
$R^4$ represents hydrogen or an alkyl or aryl group, and
A represents N or $CR^7$, wherein $R^7$ has the meaning given for $R^4$.

It is another object of the invention to provide a new process for the preparation of these novel compounds and to provide novel intermediates which are prepared during this new process.

It is another object of the invention to provide a fungicidal composition which comprises a carrier, and as active agent, at least one compound of formula I according to the invention.

It is another object of the invention to provide a method of combating fungus at a locus which comprises treating the locus with a compound of formula I according to the invention or with a composition comprising a compound of formula I according to the invention.

These and other objects and features of the invention will become more apparent from the detailed description set forth hereinbelow.

DETAILED DESCRIPTION OF THE INVENTION

It has surprisingly been found out that the novel pentafluorophenylazolopyrimidines of formula I

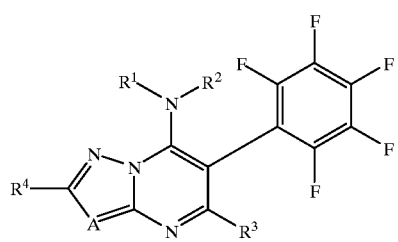

in which A and $R^1$ through $R^4$ have the meaning given above for formula I unexpectedly show excellent fungicidal activity against a broad range of fungi and are obtainable through a process which includes four synthetic steps from commercially accessible educts.

In general terms, unless otherwise stated, as used herein the term halogen atom may denote a bromine, iodine, chlorine or fluorine atom, and is especially a bromine, chlorine or fluorine atom.

Optionally substituted moieties may be unsubstituted or have from one up to the maximal possible number of substituents. Typically, 0 to 2 substituents are present.

In general terms, unless otherwise stated herein, the terms alkyl, alkenyl, alkynyl, alkadienyl as used herein with respect to a radical or moiety refer to a straight or branched chain radical or moiety. As a rule, such radicals have up to 10, in particular up to 6 carbon atoms. Suitably an alkyl moiety has from 1 to 6 carbon atoms, preferably from 1 to 3 carbon atoms. A preferred alkyl moiety is an ethyl or especially a methyl group. Suitably an alkenyl moiety has from 2 to 6 carbon atoms. A preferred alkenyl moiety is allyl or especially a 2-methylallyl group.

In general terms, unless otherwise stated herein, the term aryl, as used herein with respect to a radical or moiety refers to an aryl group having 6, 10 or 14 carbon atoms, preferably 6 or 10 carbon atoms, in particular phenyl being optionally substituted by one or more halogen atoms, nitro, cyano, alkyl, preferably $C_{1-6}$ alkyl, alkoxy, preferably $C_{1-6}$ alkoxy.

In general terms, unless otherwise stated herein, the term heteroaryl, as used herein with respect to a radical or moiety refers to a heteroaryl group having 5 or 6 ring atoms selected from carbon, nitrogen, oxygen and sulphur, at least one of which being nitrogen, oxygen or sulphur.

In general terms, unless otherwise stated herein, the term cycloalkyl, as used herein with respect to a radical or moiety refers to a cycloalkyl group having 3 to 8 carbon atoms, preferably 5 to 7 carbon atoms, in particular cyclohexyl being optionally substituted by one or more halogen atoms, nitro, cyano, alkyl, preferably $C_{1-6}$ alkyl, alkoxy, preferably $C_{1-6}$ alkoxy.

In general terms, unless otherwise stated herein, the term heterocyclyl, as used herein with respect to a radical or moiety refers to a saturated heterocyclyl group having 5 or 6 ring atoms selected from carbon, nitrogen, oxygen and sulphur, at least one of which being nitrogen, oxygen or sulphur being optionally substituted by one or more halogen atoms, nitro, cyano, alkyl, preferably $C_{1-6}$ alkyl, alkoxy, preferably $C_{1-6}$ alkoxy, in particular pyrrolodinyl, pyrrazolidin, piperidinyl, piperazinyl or morpholin-4-yl.

The invention especially relates to compounds of the general formula I in which any alkyl part of any of the groups $R^1$, $R^2$, $R^5$ and $R^6$, which may be straight chained or branched, contains up to 10 carbon atoms, preferably up to 9 carbon atoms, more preferably up to 6 carbon atoms, any alkenyl or alkynyl part of any of the substituents $R^1$ to $R^6$ contains up to 10 carbon atoms, preferably up to 9 carbon atoms, more preferably up to 6 carbon atoms, any cycloalkyl part of any of the substituents $R^1$ to $R^6$ contains from 3 to 10 carbon atoms, preferably from 3 to 8 carbon atoms, more preferably from 3 to 6 carbon atoms, any heterocyclic ring formed from $R^1$ to $R^6$ with the adjacent nitrogen atom, contains from 3 to 10 ring members, preferably from 3 to 6 carbon atoms, and any aryl part of any of the substituents $R^1$ to $R^6$ contains 6, 10 or 14 carbon atoms, preferably 6 or 10 carbon atoms, and in which each optionally substituted group independently is substituted by one or more halogen atoms or nitro, cyano, alkyl, preferably $C_{1-6}$ alkyl, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, phenyl, halo- or dihalo-phenyl or pyridyl groups. Any alkyl, alkenyl or alkynyl group may be linear or branched. A 4- to 6-membered heterocyclic group may be any heterocyclic group with 4 to 6 ring atoms, interrupted by one or more heteroatoms selected from sulfur, nitrogen, and oxygen, preferably oxygen. A halogen atom suitably denotes a fluorine, chlorine or bromine atom.

The invention especially relates to compounds of formula I in which $R^1$ represents a $C_{1-10}$ alkyl, $C_{3-6}$ cycloalkyl, $C_{3-8}$ cycloalkyl-$C_{1-6}$ alkyl, $C_{1-10}$ alkoxy-$C_{1-6}$ alkyl or phenyl group.

Preferably $R^1$ represents a $C_{1-8}$, suitably $C_{1-6}$, alkyl group, especially a branched alkyl group, more especially secondary and tertiary alkyl groups as secondary butyl, tertiary butyl and tertiary amyl groups.

The invention further especially relates to compounds of formula I in which $R^1$ and $R^2$ each independently represent a hydrogen atom, a $C_{1-12}$ alkyl, especially $C_{3-10}$ alkyl, $C_{2-6}$ alkenyl, $C_{2-6}$ alkynyl, $C_{3-8}$ cycloalkyl-$C_{1-6}$ alkyl, $C_{3-8}$ cycloalkyl, phenyl, phenyl-$C_{1-6}$ alkyl, especially benzyl, halophenyl-$C_{1-6}$ alkyl or pyridyl-$C_{1-6}$ alkyl group, or $R^1$ and $R^2$ together represent a saturated carbon chain containing three to eight carbon atoms while optionally one or more additional oxygen atoms may be present in the chain and which chain may optionally be aryl- or cycloalkyl-fused. Preferably $R^1$ and $R^2$ each independently represent a hydrogen atom, a $C_{2-12}$ alkyl, $C_{2-5}$ alkenyl, $C_{5-7}$ cyclo-$C_{1-2}$ alkyl, $C_{5-7}$ cycloalkyl or phenyl-$C_{1-2}$ alkyl group, or $R_2$ and $R_3$ together represent a saturated chain containing four or five carbon atoms while optionally additional oxygen atoms may be present and which chain optionally may be aryl- or cycloalkyl-fused, especially cyclopentyl, cyclohexyl or cycloheptyl fused, each of the above groups optionally substituted by one or more halogen atoms, especially chlorine and/or fluorine atoms, or $C_{1-4}$ alkyl, $C_{1-4}$ haloalkyl, $C_{4-6}$ cycloalkenyl or $C_{1-4}$ alkoxy groups.

In a preferred embodiment one of the radicals $R^1$ and $R^2$ is a branched $C_{3-12}$ alkyl or $C_{3-5}$ alkenyl group and the other is hydrogen or a straight chained $C_{1-4}$ alkyl group.

The invention also especially relates to compounds of formula I in which $R^2$ represents a hydrogen atom or a methyl group, preferably a hydrogen atom.

Another particular sub-group is that in which $R^1$ and $R^2$ each independently represent a hydrogen atom or a linear or branched $C_{1-12}$ alkyl group, especially a $C_{1-10}$ alkyl group, an allyl, $C_{3-7}$ cycloalkyl optionally fused with a cyclohexyl group, benzyl or phenyl group, or $R^1$ and $R^2$ together represent a saturated $C_{4-7}$ carbon chain, especially a $C_{4-6}$ carbon chain, which optionally may contain an additional oxygen atom and which optionally may be fused with a cyclohexyl ring, each of the above groups optionally substituted by a fluorine, chlorine or bromine atom or one or two methyl groups, a t-butyl, cyclohexyl, cyclohexenyl, phenyl or pyridyl group.

Particularly preferred are the compounds of the subgeneric formula IA,

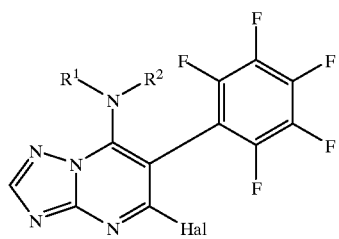

(IA)

wherein
$R^1$ and $R^2$ have the meaning given and
Hal represents halogen.

The compounds according to formula I are oils, gums, or, predominantly crystalline solid materials. They are superior through their valuable fungicidal properties. For example, they can be used in agriculture or related fields for the control of phytopathogenic fungi such as *Alternaria solani, Botrytis cinerea, Cercospora beticola, Cladosporium herbarum, Corticium rolfsii, Erysiphe graminis, Helminthosporium tritici repentis, Leptosphaeria nodorum, Micronectriella nivalis, Monilinia fructigena, Mycosphaerella ligulicola, Mycosphaerella pinodes, Pyricularia grisea f.sp. oryzae, Rhizoctonia solani* and *Sclerotinia sclerotiorum*, in particular for the control of *Pyricularia grisea f.sp. oryzae* and *Rhizoctonia solani*. The compounds of formula I according to the invention possess a high fungicidal activity within a wide concentration range and may be used in agriculture without any difficulties.

Preferred compounds are those in which $R^3$ represents a bromine or chlorine atom.

Good results in terms of control of phythopathogenic fungi are obtained with a compound as defined in formula I wherein $R^1$ represents straight chained or branched $C_1$–$C_6$-alkyl or straight chained or branched $C_2$–$C_6$-alkenyl, in particular branched $C_3$–$C_6$-alkyl or branched $C_3$–$C_6$-alkenyl, and $R^2$ represents hydrogen or $C_1$–$C_6$-alkyl, in particular straight chained $C_1$–$C_6$-alkyl, or wherein $R^1$ and $R^2$ together with the adjacent nitrogen atom represent a heterocyclic ring with 5 or 6 carbon atoms being optionally substituted with one or two $C_1$–$C_6$-alkyl groups, in particular a heterocyclic ring being optionally substituted by one or two methyl groups selected from pyrrolodinyl, pyrrazolidin, piperidinyl, piperazinyl and morpholin-4-yl.

Especially good results in terms of control of phytopathogenic fungi are obtained by using, for example, the following compounds of formula I:

5-chloro-6-(pentafluorophenyl)-7-(4-methyl-piperidin-1-yl)-[1,2,4]triazolo[1,5-a]pyrimidine;

5-chloro-6-(pentafluorophenyl)-7-(N-isopropylamino)-[1,2,4]triazolo[1,5-a]pyrimidine; and 5-chloro-6-(pentafluorophenyl)-7-(N-ethyl,N-2-methylallyl-amino)-[1,2,4]triazolo[1,5-a]pyrimidine.

The conventional methods for preparing dialkylalkyl phenylmalonates, i.e. the reaction of alkyl phenyl-acetates with carboxylates or carbondioxide in the presence of strong bases, are not applicable for the preparation of dialkyl pentafluorophenylmalonates, since the strong bases will, at least in part, substitute the fluoro atoms of the pentafluorophenyl moiety.

Therefore, the present invention further provides a process for the preparation of a compound of formula I as defined above which comprises (a) reacting hexafluorobenzene with a dilakylmalonate in the presence of a base, (b) treating the resulting 2-pentafluorophenylmalonate of formula II,

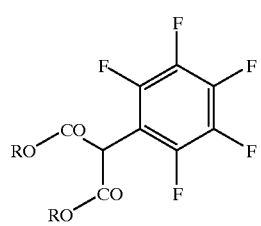

(II)

in which R is alkyl, aryl or benzyl, in particular $C_1$–$C_6$-alkyl, with a compound of formula III,

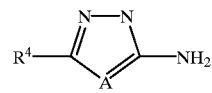

(III)

in which $R^4$ and A have the meaning given in the preceding claims, in the presence of a base, (c) treating the resulting dihydroxyazolopyrimidine of formula IV,

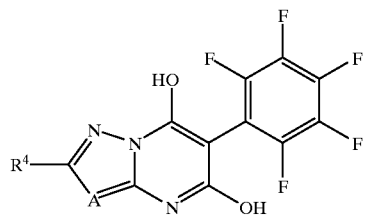

(IV)

in which $R^4$ and A have the meaning given in the preceding claims, with a halogenating agent, and (d) treating the resulting compound of the general formula V

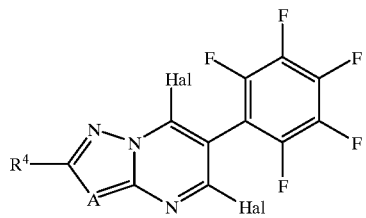

(V)

in which $R^4$ and A are as defined in any one of the preceding claims; and

Hal represents a chlorine or bromine atom, with an amine of the general formula VI

(VI)

in which $R^1$ and $R^2$ are as defined in any one of the preceding claims, to produce a compound of formula I in which $R^3$ represents a chlorine or bromine atom;

(e) if desired, reacting the compound of formula I formed in (d) with a fluorinating agent to produce a compound of formula I in which $R^3$ represents a fluorine atom, and (f) if desired, reacting the compound of formula I formed in (d) with ammonia and, subsequently, with diiodomethane in the presence of a diazotising agent to produce a compound of formula I in which $R^3$ represents an iodine atom, (g) if desired, reacting the compound of formula I formed in (d) with an amine of formula $HNR^5R^6$ to produce a compound of formula I in which $R^3$ represents—$NR^5R^6$.

The process of step (a) is conveniently carried out in the presence of a solvent. Suitable solvents include polar aprotic solvents as for example sulpholane, dimethylformamide or a mixture thereof. The reaction is suitably carried out at a temperature in the range from room temperature (about 15° C.) to the reflux temperature of the reaction mixture, the preferred reaction temperature being from 40° C. to the reflux temperature of the reaction mixture. It is also preferred that the reaction is carried out in the presence of a base. Suitable bases include tertiary amines, such as triethylamine, and inorganic bases, such as potassium carbonate or sodium carbonate.

Compounds of formula IV can be prepared by reacting 3-amino-1,2,4-triazole (A=N) or 3-amino-1,2-diazole (A=CR$^7$) of formula III with 2-penta-fluorophenyl-malonic acid ester under alkaline conditions according preferably using high boiling tertiary amines as for example tri-n-butylamine.

The process of step (c) is conveniently carried out with a brominating or chlorinating agent, such as phoshorus oxybromide or phosphorus oxychloride, neat or in the presence of a solvent. The reaction is suitably carried out at a temperature in the range from 0° C. to 150° C., the preferred reaction temperature being from 80° to 125° C.

The process of step (d) is conveniently carried out in the presence of a solvent. Suitable solvents include ethers, such as dioxane, diethyl ether and, especially, tetrahydrofuran, halogenated hydrocarbons such as dichloromethane and aromatic hydrocarbons, for example toluene. The reaction is suitably carried out at a temperature in the range from 0° C. to 70° C., the preferred reaction temperature being from 10° C. to 35° C. It is also preferred that the reaction is carried out in the presence of a base. Suitable bases include tertiary amines, such as triethylamine, and inorganic bases, such as potassium carbonate or sodium carbonate. Alternatively, an excess of the compound of formula III may serve as a base.

The process of step (e) is conveniently carried out in the presence of a solvent. Suitable solvents include sulpholane, dimethylformamide or a mixture of acetonitrile and a crown ether. If sulpholane or dimethylformamide is used as solvent, it is advantageous to use toluene as a co-solvent to aid dehydration of the fluorinating agent. The reaction is suitably carried out at a temperature in the range from room temperature (about 15° C.) to the reflux temperature of the reaction mixture, the preferred reaction temperature being from 40° C. to the reflux temperature of the reaction mixture. Suitable fluorinating agents include alkali metal fluorides, especially potassium fluoride, and antimony fluoride.

The first process of step (f) is conveniently carried out in the presence of a solvent. Suitable solvents include ethers, such as dioxane, diethyl ether and tetrahydrofuran, halogenated hydrocarbons such as dichloromethane and aromatic hydrocarbons such as toluene. The reaction is suitably carried out at a temperature in the range from 20° C. to the reflux temperature of the reaction mixture, the preferred reaction temperature being from 40° C. to the reflux temperature of the reaction mixture. It is also preferred that the reaction is carried out in the presence of a base. Suitable bases include tertiary amines, such as triethylamine, and inorganic bases, such as potassium carbonate or sodium carbonate. Alternatively an excess of ammonia may serve as base. For the diazotisation process conveniently the isolated material of the first process is used. The diazotising agent may be any alkyl ester of nitrous acid, isopentyl nitrite being especially preferred. If an alkyl ester of nitrous acid is used, this may serve as a co-solvent with the diiodomethane. The reaction is suitably carried out at a temperature from 60° C. to 120° C., the preferred reaction temperature being from 70° C. to 110° C.

The present invention further provides novel intermediates of formulae III, IV and V for the preparation of a compound of formula I as defined above:

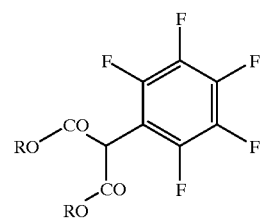

(II)

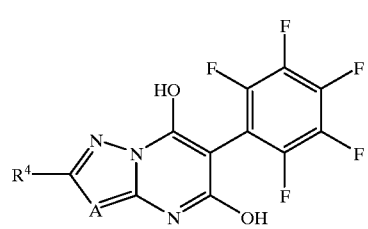

(IV)

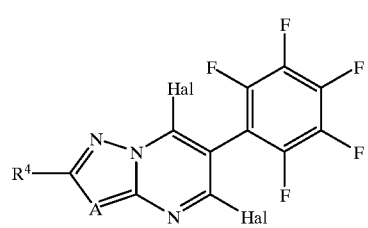

(V)

in which R, R$^4$, A and Hal have the meaning given above.

The compounds of formula I have been found to have fungicidal activity. Accordingly the invention further provides a fungicidal composition which comprises a carrier and, as active ingredient, at least one compound of formula I as defined above. A method of making such a composition is also provided which comprises bringing a compound of formula I as defined above into association with at least one carrier. Such a composition may contain a single compound or a mixture of several compounds of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally gaseous but which has been compressed to form a liquid, and any of the carriers normally used in formulating fungicidal compositions may be used.

The compositions may be manufactured into e.g. emulsion concentrates, solutions which may be sprayed directly or diluted, diluted emulsions, wettable powders, soluble powders, dusts, granulates, water-dispersible granulates, microencapsulates by well-established procedures. The form of application such as spraying, atomizing, dispersing, pouring may be chosen like the compositions according to the desired objectives and the given circumstances.

The formulations, i.e. the compositions which comprise at least one compound according to general formula I and optionally solid and/or liquid auxiliaries and adjuvants, may be prepared by well-established procedures, e.g. intensive mixing and/or grinding of the active ingredients with other substances, such as fillers, solvents, solid carriers, and optionally surface-active compounds (tensides).

Solvents may be aromatic hydrocarbons, preferably the fractions $C_8$ to $C_{12}$, e.g. xylenes or xylene mixtures, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethylene glycol mono- and dimethyl ether, ketones such as cyclohexanone, strongly polar solvents such as N-methyl 2-pyrrolidone, dimethyl sulphoxide, alkyl formamides, epoxidized vegetable oils, e.g. epoxidized coconut or soybean oil, water. Mixtures of different liquids are often suitable.

Solid carriers, which may be used for dusts or dispersible powders, may be mineral fillers, such as calcite, talc, kaolin, montmorillonite, attapulgite. The physical properties may be improved by addition of highly dispersed silica gel or highly dispersed polymers. Carriers for granulates may be porous material, e.g. pumice, broken brick, sepiolite, bentonite, non-sorptive carriers may be calcite or sand. Additionally, a multitude of pre-granulated inorganic or organic materials may be used, such as dolomite or crushed plant residues.

Fungicidal compositions are often formulated and transported in concentrated form which is subsequently diluted by the user before application. The presence of small amounts of a carrier which is a surface-active agent facilitates this process of dilution. Thus, preferably one carrier in a composition according to the invention is a surface active agent. For example, the composition may contain at least two carriers, at least one of which is a surface active agent.

Suitable surface-active substances may be non-ionogenic, anionic or cationic tensides with good dispersing, emulgating and wetting properties depending on the nature of the compound according to general formula I to be formulated. Tensides may also mean mixtures of tenides.

Suitable tensides may be so-called water-soluble soaps as well as water-soluble synthetic surface-active compounds.

Soaps usually are alkali, earth alkali or optionally-substituted ammonium salts of higher fatty acids ($C_{10}$–$C_{20}$), e.g. the sodium or potassium salts of oleic or stearic acid or of mixtures of natural fatty acids which are prepared, for example, from coconut or tallow oil. Furthermore, methyltaurine salts of fatty acids may be used.

However, so-called synthetic tensides are preferably used, especially fatty sulphonates, fatty sulphates, sulphonated benzimidazole derivatives or alkyl aryl sulphonates.

The fatty sulphates or fatty sulphonates are normally used as alkali, earth alkali or optionally-substituted ammonium salts and have an alkyl moiety of 8 to 22 carbon atoms, whereby alkyl also means the alkyl moiety of acyl residues, such as the sodium or calcium salt of lignin sulphonic acid, of sulphuric acid dodecylate or of a mixture of fatty alcohols prepared from natural fatty acids. This also includes the salts of sulphuric acid esters, sulphonic acids and adducts of fatty alcohols and ethylene oxide. The sulphonated benzimidazole derivatives preferably contain 2 sulphonic acid residues and a fatty acid residue with 8 to 22 carbon atoms. Alkyl aryl sulphonates are, for example, the sodium, calcium or triethyl ammonium salts of dodecyl benzene sulphonic acid, dibutyl naphthalene sulphonic acid or of a condensate of naphthalene sulphonic acid and formaldehyde.

Furthermore, phosphates, such as the salts of the phosphoric acid ester of a p-nonylphenol-(4–14)-ethylene oxide adduct or phospholipids, may be used.

Non-ionic tensides are preferably polyglycolether derivatives of aliphatic or cycloaliphatic alcohols, saturated or non-saturated fatty acids and alkylphenols, which have 3 to 10 glycol ether groups and 8 to 20 carbon atoms in the (aliphatic) hydrocarbon residue and 6 to 18 carbon atoms in the alkyl residue of the alkyl phenols.

Other suitable non-ionic tensides are the water-soluble, 20 to 250 ethylene glycol ether groups containing polyadducts of ethylene oxide and polypropylene glycol, ethylene diamino polypropylene glycol and alkyl polypropylene glycol with 1 to 10 carbon atoms in the alkyl moiety, the substances normally contain 1 to 5 ethylene glycol units per propylene glycol unit.

Examples of non-ionic tensides are nonylphenol polyethoxy ethanols, castor oil polyglycol ether, polyadducts of ethylene oxide and polypropylene, tributyl phenoxy polyethoxy ethanol, polyethylene glycol, octyl phenoxy polyethoxy ethanol.

Furthermore, fatty acid esters of polyoxy ethylene sorbitan, such as polyoxy ethylene sorbitan trioleate may be used.

Cationic tensides preferably are quaternary ammonium salts, which have at least one alkyl residue with 8 to 22 carbon atoms and, furthermore, low, optionally-halogenated alkyl, benzyl or hydroxyalkyl residues. The salts are preferably halides, methyl sulphates or alkyl sulphates, e.g. stearyl trimethyl ammonium chloride or benzyl bis(2-chloroethyl) ethyl ammonium bromide.

The compositions of the invention may for example be formulated as wettable powders, dusts, granules, solutions, emulsifiable concentrates emulsions, suspension concentrates and aerosols. Wettable powders usually contain 25%, 50% or 75% w/w of active ingredient and usually contain in addition to solid inert carrier, 3%–10% w/w of a dispersing agent and, where necessary, 0%–10% w/w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5%–10% w/w of active ingredient. Granules are usually prepared to have a size between 10 and 100 mesh ASTM (approx. 2.00 mm–0.15 mm), and may be manufactured by agglomeration or impregnation techniques. Generally, granules will contain 0.5%–75% active ingredient and 0–10% w/w of additives such as stabiliser, surfactants, slow release modifiers and binding agents. The so called "dry flowable powders" consist of relatively small granules having a relatively high concentration of active ingredient. Emulsifiable concentrates usually contain, in addition to a solvent or a mixture of solvents, 1%–50% w/v active ingredient, 2%–20% w/v emulsifiers and 0%–20% w/v of other additives such as stabilisers, penetrants and corrosion inhibitors. Suspension concentrates are usually compounded so as to obtain a stable, non-sedimenting flowable product and usually contain 10%–75% w/w active ingredient, 0.5%–15% w/w of dispersing agents, 0.1%–10% w/w of suspending agents such as protective colloids and thixotropic agents, 0%–10% of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick mayonnaise, like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide slow release of the fungicidal compounds into the environment of a plant which is to be protected. Such slow-release formulations could, for example, be inserted in the soil adjacent to the roots of a plant, or could include an adhesive component enabling them to be applied directly to the stem of a plant.

As commodity the compositions may preferably be in a concentrated form whereas the end-user generally employs diluted compositions. The compositions may be diluted to a concentration of 0.001% of active ingredient (a.i.). The doses usually are in the range from 0.01 to 10 kg a.i./ha.

The invention still further provides the use as a fungicide of a compound of formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes and tomatoes. The duration of the protection is normally dependent on the individual compound selected, and also a variety of external factors, such as climate, whose impact is normally mitigated by the use of a suitable formulation.

The following examples further illustrate the present invention. It should be understood, however, that the invention is not limited solely to the particular examples given below.

EXAMPLE 1

(1a) Diethyl pentafluorophenyl-malonate

A mixture of N,N-dimethylformamide (35 mL) and potassium carbonate (7.52 g, 54 mmoles) is heated to 150° C. and diethyl malonate (6.45 g, 53 mmoles) is added without further heating. Hexafluorobenzene (10 g, 53 mmoles) is added to the reaction mixture at 115° C. The resulting reaction mixture is stirred for 3 hours at 120° C. The hot solution is poured onto crushed ice (160 mL), carefully acidified with sulfuric acid and cooled to 0° C. The aqueous layer is removed and the residue is dissolved in diethyl ether. The ethereal solution is washed with aqueous sodium hydrogencarbonate and water and dried with sodium sulfate. The ether is distilled off in vacuo. The resulting product (9.5 g) contains 75% diethyl pentafluorophenyl malonate and is used as intermediate without further purification.

$^1$H-NMR data (CDCl$_3$/tetramethylsilane):

s (5.4 ppm), m (4.3–4.1 ppm), m (1.3–1.1 ppm).

(1b) 5,7-Dihydroxy-6-pentafluorophenyl-1,2,4-triazolo[1.5a]-pyrimidine

A mixture of (la) (22 mmoles), tributylamine (5.71 mL, 24 mmoles) and 2-amino-1,2,4-triazole (1.85 g, 22 mmoles) is heated to 180° C. for 6 hours. The reaction mixture is cooled down to 50° C. and an aqueous solution of sodium hydroxide (2.2 g in 25 mL) is added. The mixture is stirred for 30 minutes, the aqueous layer is separated, extracted with ether twice and acidified with concentrated hydrochloric acid. The resulting white solid is filtered off, washed with water and diisopropyl ether and dried. The resulting yellowish powder (5.2 g) decomposes at 200° C.

Elemental analysis:

|  | % C | % H | % N |
|---|---|---|---|
| calculated | 41.48 | 0.94 | 17.59 |
| found | 39.52 | 1.52 | 17.53 |

(1c) 5,7-Dichloro-6-pentafluorophenyl-1,2,4-triazolo-[1.5a]-pyrimidine

A mixture of (1b) (5.15 g, 16 mmoles) and phosphorousoxychloride (20 mL) is refluxed for 4 hours at 120° C. Dichloromethane (100 mL) is added to the reaction mixture upon cooling to room temperature. After adding water (125 mL) at temperatures below 40° C., the organic phase is separated dried with sodium sulfate and the solvent is distilled off. The resulting oil (2.6 g) is used as intermediate without further purification.

$^1$H-NMR data (CDCl$_3$/tetramethylsilane)

s (8.95 ppm).

(1d) 5- Chloro-7-N-isopropylamino-6-pentafluorophenyl-1,2,4-triazolo[1.5a]pyrimidine A mixture of isopropylamine (1.4 mmoles), triethylamine (1.4 mmoles) and dichloromethane (10 mL) is added to a mixture of (1c) (1.4 mmoles) and dichloromethane (30 mL) under stirring. The reaction mixture is stirred 16 hours at room temperature, subsequently washed two times with 1N hydrochloric acid and once with water. The organic layer is separated, dried with anhydrous sodium sulphate and the solvent is evaporated under reduced pressure. Treatment of the resulting light brown oil with tert.-butyl methyl ether (50 mL) yields white crystals (79% of th.) having a melting point of 167–168° C.

EXAMPLES 2–33

The following examples (Table I; structure and melting point) are synthesized analogously to Example 1.

TABLE I

[Structure: R¹R²N- attached to triazolo[1,5-a]pyrimidine with pentafluorophenyl and Cl substituents]

| Example | R¹ | R² | mp (°C) |
|---|---|---|---|
| 2 | —(CH$_2$)$_2$—CHCH$_3$—(CH$_2$)$_2$— | | 173–174 |
| 3 | 2-methylallyl | ethyl | 100–102 |
| 4 | cyclopentyl | H | 145–146 |
| 5 | ethyl | ethyl | 118–119 |
| 6 | allyl | ethyl | 156 |
| 7 | H | H | |
| 8 | cyclohexyl | H | 178–179 |
| 9 | 3,3,4-trimethyl-cyclopentyl | H | |
| 10 | —(CH$_2$)$_2$—CHCl—(CH$_2$)$_2$— | | |
| 11 | methyl | H | |
| 12 | ethyl | H | |
| 13 | methyl | methyl | |
| 14 | —(CH$_2$)$_6$— | | |
| 15 | —(CH$_2$)$_5$— | | 164 |
| 16 | —(CH$_2$)$_4$— | | |
| 17 | —CH$_2$—CHCH$_3$—(CH$_2$)$_3$— | | 146 |
| 18 | —CHCH$_3$—(CH$_2$)$_4$— | | |
| 19 | —(CH$_2$)$_2$—O—(CH$_2$)$_2$— | | |
| 20 | 1-ethylpropyl | H | |
| 21 | —CH$_2$—CHCH$_3$—CH$_2$—CHCH$_3$—CH$_2$— | | |
| 22 | —CH$_2$—CH=CH—(CH$_2$)$_2$— | | |
| 23 | —(CH$_2$)$_2$—N(CH$_3$)—(CH$_2$)$_2$— | | |
| 24 | —CH$_2$—C(CH$_3$)$_2$(CH$_2$)$_3$— | | |
| 25 | —CHCH$_3$—(CH$_2$)$_3$— | | |
| 26 | cyclopropyl | H | 214 |
| 27 | norbornyl | H | 194–195 |
| 28 | 1-methylpropyl | H | 122 |
| 29 | 2-methylpropyl | H | 169 |
| 30 | cycloheptyl | H | 155 |
| 31 | allyl | methyl | 140–141 |
| 32 | 2-methylpropyl | methyl | 122 |
| 33 | 1,1,3,3-tetra-methylbutyl | H | |

Biological Investigations

Determination of Minimum Inhibitory Concentration by Test Compounds in the Serial Dilution Test with Various Phytopathogenic Fungi The MIC (Minimum Inhibitory Concentration) value, which indicates the lowest concentration of the active ingredient in the growth medium which causes a total inhibition of myecelial growth, is determined by serial dilution tests using Microtiter plates with 24 or 48 wells per plate. The dilution of the test compounds in the nutrient solution and the distribution to the wells is carried out by a TECAN RSP 5000 Robotic Sample Processor. The following test compound concentrations are used: 0.05, 0.10, 0.20, 0.39, 0.78, 1.56, 3.13, 6.25, 12.50, 25.00, 50.00 and 100.00 mg/mL. For preparation of the nutrient solution, V8 vegetable juice (333 mL) is mixed with calcium carbonate (4.95 g), centrifuged, the supernatant (200 mL) diluted with water (800 mL) and autoclaved at 121° C. for 30 min.

The respective inocula (*Alternaria solani*, ALTESO; *Botrytis cinerea*, BOTRICI; *Leptosphaeria nodorum*, LEPTNO; *Phytophtora infestans*, PHYTIN; *Magnaporthe grisea oryzae*, PYRIOR; *Pyrenophora teres*, PYRNTE; *Rhizoctonia solani*, RHIZSO;) are added into the wells as spore suspensions (50 mL; 5×10$^5$/mL) or agar slices (6 mm) of an agar culture of the fungus.

After 6–12 days incubation at suitable temperatures (18–25° C.), the MIC values are determined by visual inspection of the plates (Table II; n.t.=not tested).

TABLE II

| Ex. No. | ALTESO | BOTRCI | LEPTNO | PHYTIN | PYRIOR | PYRNTE | RHISZO |
|---|---|---|---|---|---|---|---|
| 1 | 12.5 | 12.5 | 25 | 100 | 1.56 | 25 | 6.25 |
| 2 | 0.2 | 0.78 | 6.25 | 110 | 0.1 | 1.56 | 0.78 |
| 3 | 1.56 | 0.78 | 3.13 | 110 | <0.05 | 1.56 | 0.39 |
| 4 | 0.4 | 6.25 | 50 | 110 | 3.13 | 3.13 | 110 |
| 5 | 12.5 | 3.13 | 50 | 100 | 0.78 | 3.13 | 25 |
| 6 | 6.25 | 1.56 | 50 | 50 | 0.78 | 3.13 | 0.78 |
| 8 | 3.13 | 6.25 | 110 | 110 | 25 | 0.78 | 110 |
| 15 | 0.4 | 1.56 | 12.5 | 100 | 0.78 | 1.56 | 110 |
| 17 | 3.13 | 3.13 | 110 | 110 | 3.13 | 1.56 | 110 |
| 27 | 0.4 | 3.13 | 110 | 100 | 25 | 0.4 | 110 |
| 28 | 6.25 | 12.5 | 110 | 100 | 3.13 | 12.5 | 6.25 |
| 31 | 1.56 | 1.56 | 100 | 110 | 0.78 | 1.56 | 6.25 |
| 32 | 6.25 | 3.13 | 110 | 100 | 0.78 | 1.56 | 1.56 |
| standard* | 0.05 | 0.2 | 6.25 | 110 | 0.2 | 0.78 | 1.56 |

* 5-chloro-6-(2,4,6-trifluorophenyl)-7-(4-methyl-piperidin-1-yl)-[1,2,4]triazolo[1,5-a]pyrimidine which corresponds to example 2 having a 2,4,6-trifluorophenyl instead of a pentafluorophenyl group.

What is claimed:

1. A compound of the general formula

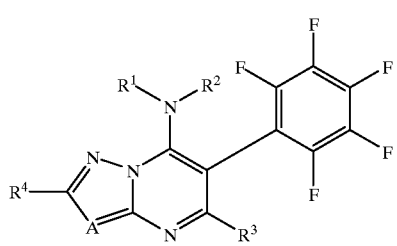

(I)

in which

R¹ and R² each independently represent hydrogen or an optionally substituted alkyl, alkenyl, alkynyl, alkadienyl, aryl, bicycloalkyl or heterocyclyl group, in which each optionally substituted group independently is substituted by one or more halogen atoms or nitro, cyano, alkyl, cycloalkyl, cycloalkenyl, haloalkyl, halocycloalkyl, alkoxy, haloalkoxy, phenyl, halo- or dihalo-phenyl or pyridyl groups, or R¹ and R² together with the adjacent nitrogen atom represent a saturated heterocyclic ring with 5 or 6 carbon atoms being optionally substituted with one or two $C_1$–$C_6$-alkyl groups, R³ represents a halogen atom or a group —NR⁵R⁶, wherein R⁵ and R⁶ each independently have one of the meanings given for R¹ and R², R⁴ represents hydrogen or an alkyl or phenyl group, and A represents N.

2. A compound according to claim 1 in which R³ represents a bromine or chlorine atom.

3. A compound according to claim 1 in which R¹ represents straight chained or branched $C_1$–$C_6$-alkyl or straight chained or branched $C_2$–$C_6$-alkenyl, and R² represents hydrogen or $C_1$–$C_6$-alkyl, or R¹ and R² together with the adjacent nitrogen atom represent a saturated heterocyclic ring with 5 or 6 carbon atoms being optionally substituted with one or two $C_1$–$C_6$-alkyl groups.

4. A compound according to claim 1 in which R⁴ is hydrogen.

5. A compound according to claim 4 in which R¹ and R² together with the adjacent nitrogen atom represent a saturated heterocyclic group selected from the group consisting of 4-methyl-piperidin-1-yl, 2-methyl-piperidin-1-yl, 3,6-dihydro-2H-pyridin-1-yl, 2-ethyl-piperidin-1-yl and azepan-1-yl.

6. A compound according to claim 1, wherein the compound is selected from the group consisting of:
5-chloro-6-(pentafluorophenyl)-7-(4-methyl-piperidin-1-yl)-[1,2,4]triazolo[1,5-a]pyrimidine
5-chloro-6-(pentafluorophenyl)-7-(N-isopropylamino)-[1,2,4]triazolo[1,5-a]pyrimidine
5-chloro-6-(pentafluorophenyl)-7-(N-ethyl,N-2-methylallylamino)-[1,2,4]triazolo[1,5-a]pyrimidine.

7. A process for the preparation of a compound of formula I

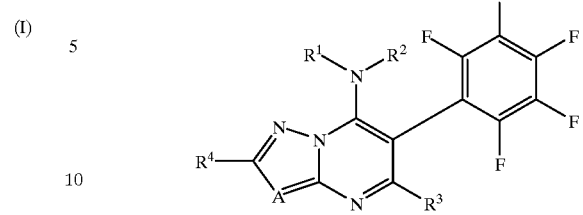

(I)

in which

R¹ and R² each independently represent hydrogen or an optionally substituted alkyl, alkenyl, alkynyl, alkadienyl, aryl, bicycloalkyl or heterocyclyl group, in which each optionally substituted group independently is substituted by one or more halogen atoms or nitro, cyano, alkyl, cycloalkyl, cycloalkenyl, haloalkyl halocycloalkyl, alkoxy, haloalkoxy, phenyl, halo- or dihalo-phenyl or pyridyl groups, or R¹ and R² together with the adjacent nitrogen atom represent a saturated heterocyclic ring with 5 or 6 carbon atoms being optionally substituted with one or two $C_1$–$C_6$-alkyl groups, R³ represents a bromine or chlorine atom, R⁴ represents hydrogen or an alkyl or phenyl group, and A represents N, which process comprises (a) reacting hexafluorobenzene with a dialkylmalonate in the presence of a base, (b) treating the resulting 2-pentafluorophenylmalonate of formula II,

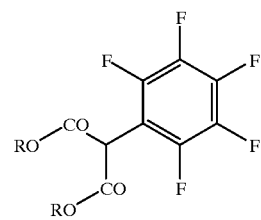

(II)

in which R is alkyl, aryl or benzyl, with a compound of formula III,

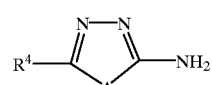

(III)

in which R⁴ and A have the meaning given above, in the presence of a base, (c) treating the resulting dihydroxyazolopyrimidine of formula IV,

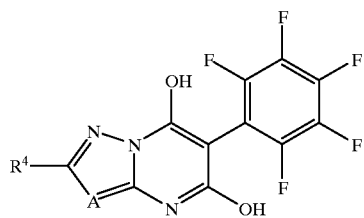

(IV)

with a halogenating agent, and (d) treating the resulting compound of formula V

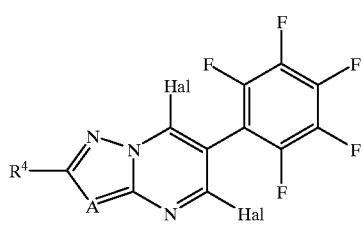

(V)

in which Hal represents a chlorine or bromine atom, with an amine of formula VI

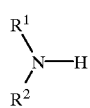

(VI)

in which $R^1$ and $R^2$ are as defined above.

8. A process according to claim 7 further comprising reacting the compound of formula I with a fluorinating agent to produce a compound of formula I wherein $R^3$ is a fluorine atom.

9. A process according to claim 7 further comprising reacting the compound of formula I with ammonia and, subsequently, diiodomethane in the presence of a diazotising agent to produce a compound of formula I wherein $R^3$ is an iodine atom.

10. A process according to claim 7 further comprising reacting the compound of formula I with an amine of the formula $HNR^5R^6$, wherein $R^5$ and $R^6$ are as defined above, to produce a compound of formula I wherein $R^3$ is $-NR^5R^6$.

11. A fungicidal composition which comprises a carrier, and as active agent, at least one compound of formula I as defined in claim 1.

12. A method of combating fungus at a locus which comprises treating the locus with a compound of formula I as defined in claim 1.

13. A method of combating fungus at a locus which comprises treating the locus with a composition as defined in claim 11.

14. A method according to claim 12 in which $R^3$ represents a bromine or chlorine atom.

15. A method according to claim 12 in which $R^1$ represents straight chained or branched $C_1$–$C_6$-alkyl or straight chained or branched $C_2$–$C_6$-alkenyl, and $R^2$ represents hydrogen or $C_1$–$C_6$-alkyl, or $R^1$ and $R^2$ together with the adjacent nitrogen atom represent a saturated heterocyclic ring with 5 or 6 carbon atoms being optionally substituted with one or two $C_1$–$C_6$-alkyl groups.

16. A method according to claim 12 in which $R^4$ is hydrogen.

17. A method according to claim 16 in which $R^1$ and $R^2$ together with the adjacent nitrogen atom represent a saturated heterocyclic group selected from the group consisting of 4-methyl-piperidin-1-yl; 2-methyl-piperidin-1-yl; 3,6-dihydro-2H-pyridin-1-yl; 2-ethyl-piperidin-1-yl; and azepan-1-yl.

18. A method according to claim 12, wherein the compound is selected from the group consisting of
5-chloro-6-(pentafluorophenyl)-7-(4-methyl-piperidin-1-yl)-[1,2,4]triazolo-[1,5-a]pyrimidine;
5-chloro-6-(pentafluorophenyl)-7-(N-isopropylamino)-[1,2,4]triazolo[1,5-a]pyrimidine; and
5-chloro-6-(pentafluorophenyl)-7-(N-ethyl, N-2-methylallylamino)-[1,2,4]triazolo-[1,5-a]pyrimidine.

* * * * *